United States Patent
Clark et al.

(10) Patent No.: US 6,207,187 B1
(45) Date of Patent: Mar. 27, 2001

(54) COMPOSITIONS BASED ON TOCOPHEROLS

(75) Inventors: James P. Clark, Naperville; Manfred S. Dunker, Palos Park, both of IL (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 08/849,979

(22) PCT Filed: Dec. 22, 1995

(86) PCT No.: PCT/US95/16770

§ 371 Date: Aug. 22, 1997

§ 102(e) Date: Aug. 22, 1997

(87) PCT Pub. No.: WO96/19216

PCT Pub. Date: Jun. 27, 1996

Related U.S. Application Data

(63) Continuation-in-part of application No. 08/362,618, filed on Dec. 22, 1994, now abandoned.

(51) Int. Cl.[7] .......................... A61K 9/48; A61K 31/355
(52) U.S. Cl. .......................................... 424/455; 424/456
(58) Field of Search .................................. 424/451, 456, 424/464, 455

(56) References Cited

U.S. PATENT DOCUMENTS

| | | | |
|---|---|---|---|
| 4,088,778 | 5/1978 | Igarashi et al. | 424/284 |
| 4,612,194 | 9/1986 | Ismail | 424/195 |
| 4,873,088 * | 10/1989 | Mayhew et al. | 424/450 |
| 5,080,886 | 1/1992 | Mickle et al. | 424/10 |
| 5,114,957 * | 5/1992 | Hendler et al. | 514/356 |
| 5,157,132 | 10/1992 | Tan et al. | 549/413 |
| 5,190,618 | 3/1993 | Top et al. | 203/34 |
| 5,217,992 | 6/1993 | Wright et al. | 514/458 |
| 5,393,776 | 2/1995 | Pearce | 514/486 |

FOREIGN PATENT DOCUMENTS

401079119 * 3/1989 (JP) .............................. A61K/31/56

OTHER PUBLICATIONS

Remington's Pharmaceutical Sciences, 18th Edition, pp. 1008–1009.

M. Ivey & G. Elmer, "Nutritional Supplement, Mineral, And Vitamin Products", Handbook Of Nonprescription Drugs, 9th Edition, American Pharmaceutical Association, Washington, D.C., 1990, pp. 447–527.

Medline Abstracts, issued 1991, Tan, D.T., et al., "Effect Of A Palm–Oil–Vitamin E Concenrate On The Serum And Lipoprotein Lipids In Humans", Abstract No. 91189080, Am. J. Clin. Nutr. vol. 53 (4 Suppl), 1027s–1030s).

Tan, et al., "Effect of a Palm–oil–vitamin E concentrate on the serum and lipoprotein lipids in humans", vol. 53, American Society for Clinical Nutrition, Apr., 1991, pp. 1027S–1030S.

Stampfer et al., "Vitamin E Consumption and The Risk of Coronary Disease in Women", *The New England Journal of Medicine*, 328: 1444–9 (1993).

Rimm et al., "Vitamin E Consumption and The Risk of Coronary Disease in Men", *The New England Journal of Medicine*, 328: 1450–6 (1993).

Kardinaal et al., "Antioxidants in Adipose Tissue and Risk of Myocardial Infarction: The Euramic Study," *Lancet*, 342:1379–84 (1993).

Gaziano et al., "Beta Carotene Therapy for Chronic Stable Angina", *Circulation*, 82:III, Abstract No. 0796 (1990).

Singh et al., "A Current Perspective on Nutrition and Exercise", American Institute of Nutrition, 1992.

\* cited by examiner

Primary Examiner—James M. Spear
(74) Attorney, Agent, or Firm—John E. Drach; Glenn E. J. Murphy; Aaron E. Ettelman

(57) ABSTRACT

A method for protecting the body against oxidation of low density lipoproteins by the oral administration of a protective amount of a natural tocopherol and tocopherol acetate or tocopherol succinate.

2 Claims, No Drawings

COMPOSITIONS BASED ON TOCOPHEROLS

CROSS-REFERENCE TO RELATED APPLICATIONS

This application is a 35 U.S.C. §371 national stage application of International Application No. PCT/US95/16770, filed on Dec. 22, 1995, and a continuation-in-part of U.S. application Ser. No. 08/362,618, filed on Dec. 22, 1994 (now abandoned).

FIELD OF THE INVENTION

The present invention relates to methods of treatment and more particularly it relates to protecting the body from chronic diseases by the administration of a combination of naturally occurring tocopherols with tocopherol succinate or tocopherol acetate. This invention also includes within its scope pharmaceutical compositions containing natural tocopherols and its succinate or acetate for administration to a mammal, including humans, in need of such treatment.

BACKGROUND OF THE INVENTION

Tocopherols (Vitamin E) and in particular alpha-tocopherol is known to be essential in humans as well as other species for normal reproduction, normal development of muscles, resistance of erythrocytes to hemolysis, and as an antioxidant. See, for example, U.S. Pat. No. 4,612,194 which discloses several uses of Vitamin E as well as the dose regimen for a variety of clinical conditions. Vitamin E is usually combined with other vitamins and essential elements and marketed as dietary supplements. Singh et al., "A Current Perspective on Nutrition and Exercise" published by American Institute of Nutrition 1992, describes the protective effects of Vitamin E against free radical damage.

Another approach is described in the articles "Vitamin E Consumption And The Risk Of Coronary Disease In Women" by Stampfer et al., *The New England Journal of Medicine*, 328: 1444–9 (1993), and "Vitamin E Consumption And The Risk of Coronary Heart Disease In Men" by Rimm et al., *The New England Journal of Medicine*, 328: 1450–6 (1993), wherein it was disclosed that oxidation of low-density lipoprotein (LDL) plays a role in atherosclerosis. Thus, the oxidation of LDL increases their incorporation into the arterial intima which is an essential step in atherogenesis.

A variety of dietary and drug regimens have been developed or proposed which would block the oxidative modification of LDL. These regimen usually include the ingestion of vitamin E alone.

Thus, in the articles identified above, the investigators studied the effect of administering vitamin E and the risk of developing coronary disease and observed that the use of vitamin E supplements in middle-aged women is associated with a reduced risk of coronary heart disease. Similarly, an association between a high intake of vitamin E and a lower risk of coronary heart disease was also observed in men.

In another study reported in *Lancet*, 342: 1379–84 (1993), it was observed that high beta-carotene intake reduced the risk of myocardial infarction. Beta-carotene has also been suggested as useful in reducing vascular events in patients with chronic stable angina. See, Gaziano et al., "Beta Carotene Therapy for Chronic Stable Angina," *Circulation*, 82:III, Abstract No. 0796 (1990).

Surprisingly, the present inventors have now discovered that combinations of naturally occurring tocopherol with tocopherol succinate or acetate are suitable for the protection of the body from chronic diseases, which include for example coronary artery disease, atherosclerosis and the like. This protective action is based on the observation that these two compounds prevent or retard the oxidation of low-density lipoprotein (LDL) thereby protecting the body from the development of atherosclerosis.

SUMMARY OF THE INVENTION

It is therefore an object of the present invention to provide a method for protection of the body from chronic diseases.

It is another object of this invention to provide compositions containing naturally occurring tocopherols with tocopherol succinate or acetate for the prevention or management of chronic diseases.

The term tocopherol is meant to embrace all four naturally occurring tocopherols, i.e., alpha, beta, gamma and delta. While in the present invention, d-alpha tocopherol is preferred but dl-alpha tocopherol may be employed as well. For purposes of this invention, "chronic diseases" is meant to include ischemic heart disease, hypertension, hypercholesterolemia and the like. These are not life threatening diseases but if untreated they could lead to serious clinical manifestations.

DESCRIPTION OF THE PREFERRED EMBODIMENT OF THE INVENTION

In the prior art, various dosage forms of vitamin E has been suggested. For example, 750 mg of vitamin over a period of three to six months for a variety of clinical conditions was disclosed in U.S. Pat. No. 4,612,194. In combination products with other vitamins, vitamin E in the range of 150 mg to 500 mg per dosage unit, has been marketed.

It is the natural compounds which are useful in the practice of the present invention. Natural tocotrienols and natural tocopherols are derived from vegetable oils. Soy oil is the most widely used source. Sunflower, corn, peanut, rapeseed and cottonseed oils may also be used. Natural tocotrienol and natural tocopherols are very different from that produced by chemical synthesis, i.e., synthetic "vitamin E." While the definition of vitamin E is not consistent, for the purposes of the present invention, vitamin E refers to both tocotrienols and tocopherols.

Synthetic vitamin E is a mixture of eight different stereoisomers, only one of which is molecularly equivalent to natural vitamin E. The other seven stereoisomers have a lower biological activity. The mammalian body prefers the natural stereoisomer.

Natural vitamin E is recognized as having 36 percent greater potency than synthetic vitamin E. Recent studies suggest that natural vitamin E is probably twice as effective as synthetic vitamin E.

Natural vitamin E also remains in the body much longer than synthetic vitamin E. The seven synthetic stereoisomers are secreted into the bile and then into the intestine for removal from the body. The natural vitamin E stereoisomer, on the other hand, is returned to the bloodstream in the form of low density lipoproteins.

Any natural tocopherol or tocotrienol, its ester or compounds convertible to either tocopherols or their esters are suitable for use in the practice of the present invention.

The prior art has failed to appreciate any benefit associated with the administration of tocotrienols and tocopherols to a mammal, including humans, for the prevention or treatment of chronic diseases. Further, the prior art has heretofore never recognized any benefit for such a method using natural tocopherols or natural tocotrienols.

While the exact mechanism is unknown, the present inventors have found that the combination of natural tocopherol and/or natural tocotrienol with tocopherol succinate or acetate taken over a sustained period of time, e.g., after several months, exhibits a protective action. Thus, in some instances the symptoms of the chronic diseases seem to be reduced as exemplified by lower cholesterol level in the serum, and increased exercise tolerance.

The oral compositions can be made by conventional compounding procedures known in the pharmaceutical art, that is, by mixing the active substances with edible pharmaceutically acceptable non-toxic inert, solid or liquid carriers and/or excipients suitable for systemic administration and conventionally used in oral dosage forms. Additionally, edible, non-toxic pharmaceutically acceptable stabilizers usually used as stabilizers in oral dosage forms or edible, non-toxic pharmaceutically acceptable salts thereof as well as ascorbic acid can be included in the compositions. All the above carriers, excipients and stabilizers are intended to include only those suitable for oral administration and all are conventional and known to the pharmaceutical compounding art.

Among the dosage forms particularly suitable for the method of this invention are soft gelatin capsules. Thus, from 100 mg to 500 mg of natural tocopherol or tocotrienol are mixed with from 100 mg of the selected ester with a suitable diluent such as a vegetable oil and then encapsulated in a soft gelatin capsule. Other dosage forms include for example suspensions in which the tocopherols and the selected ester is suspended or dissolved in alcohol with excipients such as flavoring agents.

The initial dose of the combination of naturally occurring tocopherol with the ester is in the range of 100 mg to 1000 mg. The dose regimen may be adjusted by the clinician based on his clinical observations but also the weight, age and gender of the subject being treated. While the method of the present relates to the use of tocopherol and the ester, obviously they may be combined with other therapeutic agents to broaden its clinical use.

In order to illustrate the practice of the present invention, the following non-limiting example is provided. It will be appreciated that a vast number of additional compositions fall within the scope of the present invention. The Example is provided by way of illustration only and is not intended to limit the invention in any way.

EXAMPLE 100 mg of natural tocopherol are mixed with 200 mg of tocopherol acetate and 200 mg of corn oil and encapsulated into soft gelatin capsule each capsule weighing about 500 mg.

What is claimed is:

1. A method for retarding the oxidation of LDL in a mammal, said method comprising administering to a mammal an effective amount of a combination of natural tocopherol with tocopherol acetate or tocopherol succinate to retard oxidation of LDL.

2. A method for retarding the oxidation of LDL in a mammal, said method comprising administering to a mammal a daily dosage of approximately 100 mg to 1000 mg of a combination of natural tocopherol with tocopherol acetate or tocopherol succinate.

* * * * *